United States Patent [19]

Aubert et al.

[11] Patent Number: 4,529,596

[45] Date of Patent: Jul. 16, 1985

[54] THIENO [3,2-c] PYRIDINE DERIVATIVES AND THEIR THERAPEUTIC APPLICATION

[75] Inventors: Daniel Aubert, Plaisance Du Touch; Claude Ferrand, Ramonville Saint-Agne; Jean-Pierre Maffrand, Garonne, all of France

[73] Assignee: Sanofi, S.A., Toulouse, France

[21] Appl. No.: 510,582

[22] Filed: Jul. 5, 1983

[30] Foreign Application Priority Data

Jul. 13, 1982 [FR] France .............................. 82 12599

[51] Int. Cl.³ .................. A61K 31/435; C07D 495/04
[52] U.S. Cl. .................................... 514/231; 514/301; 544/127; 544/362; 546/114
[58] Field of Search ................ 546/114; 544/362, 127; 424/248.51, 250, 256

[56] References Cited

U.S. PATENT DOCUMENTS 2,527,574  10/1950  Rieveschl, Jr. ..................... 546/238

*Primary Examiner*—Henry R. Jiles
*Assistant Examiner*—Bernard L. Dentz
*Attorney, Agent, or Firm*—Weiser & Stapler

[57] ABSTRACT

This invention relates to new thieno [3,2-c] pyridine derivatives having the formula:

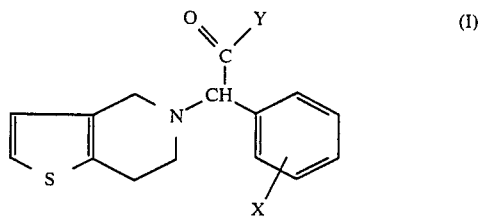

in which:

Y represents the OH group or an OR group in which R is a straight or branched lower alkyl radical, or Y represents a group

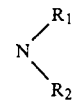

in which $R_1$ and $R_2$ are each independently of each other, hydrogen or a straight or branched lower alkyl group; or $R_1$ and $R_2$ form together and with the nitrogen atom to which they are attached a heterocycle which may include a second heteroatom such as oxygen or nitrogen, wherein the latter may be substituted by a lower alkyl or benzyl radical which may be substituted; and X represents hydrogen, a halogen or a lower alkyl radical; and their addition salts with pharmaceutically acceptable mineral or organic acids if Y represents the group OR or

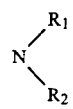

or with mineral bases if Y represents OH, as well as the two enantiomers or their mixture.

The invention also relates to the preparation process of new thieno [3,2-c] pyridine derivatives and to their therapeutic application as blood-platelet aggregation inhibiting agents and antithrombotics.

12 Claims, No Drawings

THIENO [3,2-c] PYRIDINE DERIVATIVES AND THEIR THERAPEUTIC APPLICATION

This invention relates to new thieno[3,2-c]pyridines, to a process for their preparation and to their therapeutic applications. The new derivatives of this invention have the following general formula:

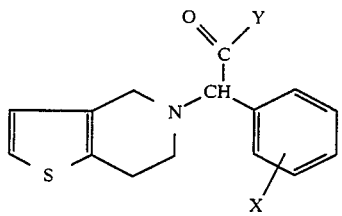

in which:

Y represents the OH group or an OR group in which R is a straight or branched lower alkyl radical, or Y represents a group

in which $R_1$ and $R_2$ are each independently of each other hydrogen or a straight or branched lower alkyl group; or $R_1$ and $R_2$ form together and with the nitrogen to which they are attached a heterocycle which may include a second heteroatom such as oxygen or nitrogen, wherein the latter may be substituted by a lower alkyl or benzyl radical which may be substituted; and X represents hydrogen, a halogen or a lower alkyl radical.

These compounds having an asymmetrical carbon may exist in the form of two enantiomers. The invention relates both to each enantiomer and their mixture.

The invention also includes addition salts with pharmaceutically acceptable mineral or organic acids if Y represents the groups OR or

or with mineral bases if Y represents OH.

A lower alkyl radical is understood to mean a $C_1$–$C_4$ saturated hydrocarbon chain.

The invention also relates to a process for the preparation of compounds of the formula (I) as defined above, wherein the esters of the invention in which Y represents an OR group as defined above are prepared by condensation of 4,5,6,7-tetrahydro-thieno[3,2-c]-pyridine, having the following formula:

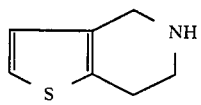

with an α-chlorophenyl acetate having the following formula

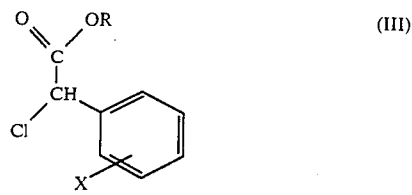

in which R and X have the above-defined meanings. Acids of formula (I), in which Y represents OH, are obtained by saponification.

To prepare the amides, in which Y represents a group

in which $R_1$ and $R_2$ have the above-defined meanings or even some esters of formula (I), the acid of formula (I)(R=OH) is reacted, after activation if required, either with the amine

or with the alcohol R—OH.

The α-halogenated esters of the formula (III) are prepared using known methods (E. L. ELIEL, M. T. FISK and T. PROSSER, Organic Syntheses, Coll. Vol. IV, J. WILEY and SONS, Inc. New York, 1963, p. 169).

Although it is possible to obtain all the esters of formula (I) by the reaction between the compounds of formulae (II) and (III), for economic reasons it is preferable to prepare certain higher esters of the formula (I) from the acid of formula (I) and alcohol (R—OH).

The condensation of the tetrahydro-thieno-pyridine with the ester of formula (III) is effected in the presence of an alkali metal carbonate, such as potassium carbonate for example, in an inert solvent such as dimethylformamide, tetrahydrofuran or 1,2-dimethoxy ethane, at temperatures between 60° C. and the boiling point of the solvent.

The saponification of the ester of formula (I) in which R is methyl or ethyl is effected by an alkali metal hydroxide such as sodium or potassium hydroxide in a hydroalcoholic solvent, at temperatures between room temperature and the boiling point of the solvent.

Activation of the acid of formula (I) may be obtained by treatment with ethyl chloroformate in the presence of a slight excess of triethylamine at temperatures between −5° C. and 0° C. in an inert solvent such as chloroform, 1,2-dimethoxy ethane or tetrahydrofuran.

A mixed anhydride having the following formula:

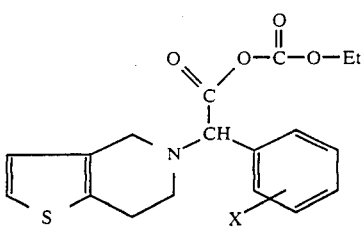 (IV)

is formed and if treated in situ with a slight excess either of alcohol or amine, at temperatures between 10° C. and room temperature, the esters or amides of the formula (I) will be formed respectively.

The activation of the acid of formula (I) may also be obtained in different ways: the amides of formula (I) were also thus prepared by condensing the acid (I) with the amine

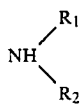

in the presence of dicyclohexycarbodiimide in solution in 1,2-dichloro-ethane.

The esters of formula (I) may also be obtained in the conventional manner by condensing the corresponding acid and alcohol (ROH) in the presence of hydrochloric gas or thionyl chloride.

The following non-limiting Examples are given to illustrate the invention.

EXAMPLE 1

Methyl α-[4,5,6,7-tetrahydro-thieno[3,2-c]-5-pyridyl]-o.chlorophenylacetate ($R_1=-CH_3$; X=2-Cl) derivative No. 1.

3.47 g (0.144 mole) of methyl 2-chloro-o.chlorophenylacetate and 19.82 g (0.144 mole) of potassium carbonate are added to a 20 g (0.144 mole) solution of 4,5,6,7-tetrahydro thieno[3,2-c]pyridine in 200 ml of dimethylformamide. The solution is then heated for four hours at 90° C. The reaction mixture is cooled to room temperature, the mineral salts are filtered and the solvent is evaporated. The residue is taken up in water and then extracted with ethylic ether. The ether extracts are washed with water, dried over sodium sulphate and evaporated, to give a yellow oil which is purified by means of its hydrochloride. White crystals: M.p.=130°-140° C. (ethylacetate, isopropanol). Yield: 45%.

EXAMPLE 2

Methyl α-[4,5,6,7-tetrahydro-thieno[3,2-c]-5-pyridyl]phenylacetate ($R_1=-CH_3$; X=H) derivative No. 2.

This compound is prepared by the same procedure described in Example 1 by alkylation of the 4,5,6,7-tetrahydro thieno[3,2-c]pyridine with methyl 2-chlorophenylacetate. Hydrochloride; white crystals: softening point=200° C. (ethanol). Yield: 50%.

EXAMPLE 3

Methyl α-[4,5,6,7-tetrahydro-thieno[3,2-c]-5-pyridyl]-o.fluorophenylacetate ($R_1=-CH_3$; X=2-F) derivative No. 3.

This compound is prepared by the same procedure as described in Example 1 by alkylation of 4,5,6,7-tetrahydro thieno[3,2-c]pyridine with methyl 2-chloro-o.fluoro-phenylacetate. Hydrochloride; white crystals: M.p.=100° C. Yield: 76.5%.

EXAMPLE 4

Ethyl α-[4,5,6,7-tetrahydro-thieno[3,2-c]-5-pyridyl]-o.methyl-phenylacetate. ($R_1=-CH_2-CH_3$; X=2-$CH_3$) derivative No. 4.

This compound is prepared by the procedure described in Example 1 by alkylation of 4,5,6,7-tetrahydro thieno[3,2-c]pyridine with ethyl 2-chloro-o.methyl-phenylacetate. Bisulphate; white crystals: M.p.=188°-190° C. (isopropanol). Yield: 54%.

EXAMPLE 5

α-[4,5,6,7-tetrahydro-thieno[3,2-c]-5-pyridyl]-o.chlorophenylacetic acid. ($R_1=H$; X=2-Cl) derivative No. 5.

A mixture of 157.9 g of ethyl α-[4,5,6,7-tetrahydro-thieno[3,2-c]-5-pyridyl]-o.chloro-phenylacetate and 100 ml of a 30% sodium hydroxide solution in 600 ml of ethanol is heated under reflux for 2 hours 30 minutes. After evaporation of the ethanol, the mixture is acidified with glacial acetic acid and extracted with methylene chloride. The organic phase is washed with water, dried over sodium sulphate and then evaporated. After recrystallization in water, the product is isolated in monohydrate form. White crystals; Softening point=125° C. (water). Yield: 46%.

EXAMPLE 6

α-[4,5,6,7-tetrahydro-thieno[3,2-c]-5-pyridyl]-phenylacetic acid. ($R_1=H$; X=H) derivative No. 6.

This compound is prepared by the procedure described in Example 9 by saponification of ethyl α-[4,5,6,7-tetrahydro-thieno[3,2-c]-5-pyridyl]-phenylacetate. The product is purified by means of its sodium salt.

White crystals: M.p.=210°-215° C. (ethanol, methanol).

Yield: 74%.

EXAMPLE 7 n-Propyl α-[4,5,6,7-tetrahydro-thieno[3,2-c]-5-pyridyl]-o.chloro phenylacetate. ($R_1=-CH_2-CH_2-CH_3$; X:2-Cl) derivative No. 7.

A stream of hydrochloric gas is bubbled through a 10 g (0.0306 mole) solution of α-[4,5,6,7-tetrahydro-thieno[3,2-c]-5-pyridyl]-o.chlorophenylacetic acid monohydrate (Example 5) for 12 hours in 100 ml of n-propanol which is refluxed. The mixture is evaporated and the residue is taken up in water, basified with sodium bicarbonate and extracted with ethylic ether. The ether extracts are washed with water, dried over sodium sulphate and evaporated to give a yellow oil which is purified by means of its bisulphate. White crystals: M.p.=146° C. (crude) Yield: 78%.

EXAMPLE 8 n-Butyl α-[4,5,6,7-tetrahydro-thieno[3,2-c]-5-pyridyl]-o.chloro-phenylacetate. ($R_1 = -CH_2-CH_2-CH_2 13 CH_3$; X=2-Cl) derivative No. 8.

This compound is prepared by the procedure described in Example 5 by esterification of α-[4,5,6,7-tetrahydro-thieno[3,2-c]-5-pyridyl]-o.-chloro-phenylacetic acid monohydrate (Example 5) with n-butanol. Purified using the bisulphate; white crystals; M.p.=155° C. Yield: 79.5%.

EXAMPLE 9

Isopropyl α-[4,5,6,7-tetrahydro-thieno[3,2-c]-5-pyridyl]-o.-chloro-phenylacetate.

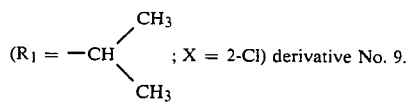

2 ml of thionyl chloride are added dropwise to a 1 g (0.0031 mole) suspension of α-[4,5,6,7-tetrahydro-thieno[3,2-c]-5-pyridyl]-o.chloro-phenylacetic acid monohydrate (Example 5) in 20 ml of isopropanol cooled to −10° C. The reaction mixture is then refluxed for 6 hours. After evaporation, the residue is taken up in water, basified with sodium bicarbonate and extracted with methylene chloride. The organic phase is washed with water, dried over sodium sulphate and evaporated. A colourless resin is collected and purified using the bisulphate.

White crystals: softening point=140°–150° C.
Yield: 44%.

EXAMPLE 10

Ethyl α-[4,5,6,7-tetrahydro-thieno[3,2-c]-5-pyridyl]-o.chloro-phenylacetate. ($R_1 = CH_2-CH_3$; X=2-Cl) derivative No. 10.

4.86 ml (0.051 mole) of ethylchloroformate are added dropwise to a 15 g (0.046 mole) solution of α-[4,5,6,7-tetrahydro-thieno[3,2-c]-5-pyridyl]-o.phenylacetic acid monohydrate (Example 5) and 7.12 ml (0.051 mole) of triethylamine in 150 ml of chloroform, cooled to a temperature between −5° and 0° C. The mixture is then allowed to return to room temperature and is stirred for 30 minutes. The reaction mixture is then cooled to a temperature of around 10° C. and 30 ml of ethanol are added dropwise. The reaction mixture is stirred at room temperature for one night and is then washed with water. The organic phase, dried over sodium sulphate, is evaporated to give a colourless oil which is purified by means of its hydrobromide.

White crystals: M.p.=180° C.
Yield: 94%.

EXAMPLE 11

N,N-dimethyl α-(4,5,6,7-tetrahydro-thieno(3,2-c)-5-pyridyl)-o.chloro-phenylacetamide.

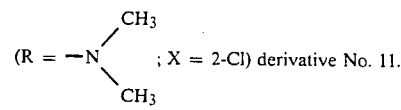

9.72 ml (0.102 mole) of ethyl chloroformate are added dropwise to a 30 g (0.092 mole) solution of α-(4,5,6,7-tetrahydro-thieno(3,2-c)-5-pyridyl)-o.chloro-phenylacetic acid monohydrate and 14.24 ml (0.102 mole) of triethylamine in 300 ml of chloroform, cooled to a temperature between −5° and 0° C. The mixture is then allowed to return to room temperature and is stirred for 30 minutes. The reaction mixture is then cooled to a temperature of around 10° C. and 4.57 ml (0.102 mole) of dimethylamine are added dropwise to 60 ml of chloroform and the mixture is stirred at room temperature for one night. Water is added, the mixture is decanted, and the organic phase is dried over sodium sulphate and evaporated. A colourless resin is collected, which then crystallizes.

White crystals: M.p.=95°–100° C. (isopropylic ether).
Yield: 49%.

EXAMPLE 12

1-[(2-chloro phenyl)-(4,5,6,7-tetrahydro-thieno(3,2-c)-5-pyridyl)acetyl]-pyrrolidine.

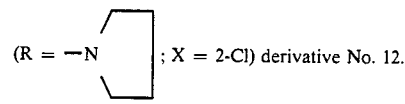

This compound is prepared by the procedure described in Example 11 by condensing α-(4,5,6,7-tetrahydro-thieno(2,3-c)-5-pyridyl]-o.chloro-phenylacetic acid monohydrate with pyrrolidine.

White crystals: M.p.=130° C. (isopropylic ether).
Yield: 61.5%.

EXAMPLE 13

1-[(2-chloro-phenyl)-(4,5,6,7-tetrahydro-thieno(3,2-c)-5-pyridyl)-acetyl]-morpholine.

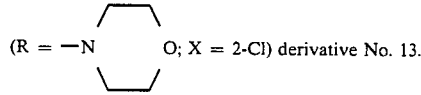

2.67 g (0.031 mole) of morpholine are added to a 10 g (0.031 mole) solution of α-[4,5,6,7-tetrahydro-thieno(3,2-c)-5-pyridyl]-o.chloro-phenylacetic acid monohydrate and 13.3 g (0.064 mole) of dicyclohexylcarbodiimide in 100 ml of 1,2-dichloro ethane and the mixture is stirred at room temperature for one night. The mixture is evaporated then taken up with 2N hydrochloric acid and ethylic ether. After filtering the dicyclohexylurea formed, the filtrate is decanted and the aqueous phase is basified with 2N sodium hydroxide then extracted with methylene chloride. The organic phase is washed with water, dried over sodium sulphate and evaporated to give a yellow resin which is purified by means of its hydrochloride hemihydrate.

White crystals: M.p.=215°-255° C. (isopropanol).
Yield: 71%

EXAMPLE 14

1-[(2-chloro phenyl)-(4,5,6,7-tetrahydro-thieno(3,2-c)-5-pyridyl)-acetyl]-piperidine.

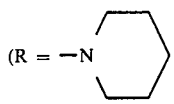; X = 2-Cl) derivative No. 14.

This compound is prepared by the procedure described in Example 13 by condensing α-[4,5,6,7-tetrahydro-thieno(3,2-c)-5-pyridyl]-o.chloro-phenylacetic acid monohydrate with piperidine.

White crystals: M.p.=139° C. (isopropanol).
Yield: 51.5%.

The following compounds were prepared by the process described in Example 11:

[α-(4,5,6,7-tetrahydro-thieno(3,2-c)-5-pyridyl]-o.chlorophenylacetamide. (R=—NH₂; X=2-Cl). derivative No. 15.

White crystals; M.p.=126°-128° C. (isopropylic ether-isopropanol).
Yield: 46%.

4-benzyl-1-[(2-chloro-phenyl)-(4,5,6,7-tetrahydro-thieno(3,2-c)-5-pyridyl)acetyl]-piperazine.

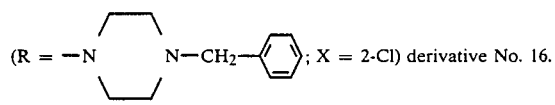; X = 2-Cl) derivative No. 16.

oxalate: white crystals: M.p.=178° C. (ethanol).
Yield: 82.5%.

N,N-dimethyl[α-(4,5,6,7-tetrahydro-thieno(3,2-c)-5-pyridyl)-o.fluoro-phenylacetamide.

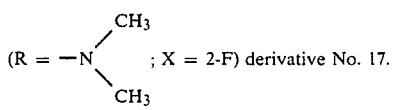; X = 2-F) derivative No. 17.

Slightly yellowish powder; M.p.=125° C. (isopropylic ether-isopropanol).
Yield: 41%.

N-methyl-[α-(4,5,6,7-tetrahydro-thieno(3,2-c)-5-pyridyl)-o.chloro-phenylacetamide. (R=NH—CH₃; X=2-Cl)—derivative No. 18.

White crystals: M.p.=137° C. (isopropanol).
Yield: 85.5%.

N-butyl[α-(4,5,6,7-tetrahydro-thieno(3,2-c)-5-pyridyl)-o.chloro-phenylacetamide. (R=—NH—(CH₂)₃—CH₃; X=2-Cl)—derivative No. 19.

White crystals: M.p.=101° C. (isopropylic ether).
Yield: 65%.

N,N-dimethyl[α-(4,5,6,7-tetrahydro-thieno(3,2-c)-5-pyridyl)phenylacetamide.

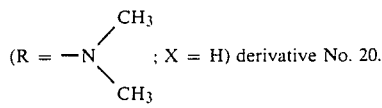; X = H) derivative No. 20.

White crystals: M.p.=138° C. (isopropylic ether).
Yield: 39%.

N,N-dimethyl[α-(4,5,6,7-tetrahydro-thieno(3,2-c)-5-pyridyl)-o.methyl-phenylacetamide.

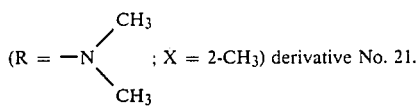; X = 2-CH₃) derivative No. 21.

White crystals: M.p.=119° C. (hexane).
Yield: 15%

The results of pharmacological and toxicological tests reported below demonstrate the properties of the derivatives of the invention both in terms of toxicity and tolerance, and the activity levels of the derivatives, especially their inhibiting action on blood-platelet aggregation and anti-thrombotic activity.

Thus, the invention also relates to a therapeutic composition having in particular an inhibiting action on blood-platelet aggregation and anti-thrombotic action, wherein the active ingredient is a derivative of the formula (I) or an addition salt thereof with a pharmaceutically acceptable mineral or organic acid if Y represents the groups OR or

and with a mineral base if Y is OH.

TOXICOLOGICAL INVESTIGATION

The compounds of the invention exhibit an excellent tolerance and a low toxicity.

In addition, the tests carried out on acute, chronic, sub-chronic and delayed toxicity in various animal species showed no local or general reaction, no disturbances or abnormalities in the biochemical, macroscopic and microscopic examinations performed during this experiment.

PHARMACOLOGICAL INVESTIGATION (1) Inhibiting action on blood-platelet aggregation This experiment was performed on rats. The compound to be tested was administered orally in the form of a suspension in gum arabic to the rats over a 3-day period 48 hours, 24 hours and 2 hours before taking a 4 ml blood sample from the animals using Renaud's method from their jugular veins under anaesthetic. The citrated blood was used in the aggregation determinations.

(a) Determination of A.D.P.-induced blood-platelet aggregation.

2 ml of citrated blood were poured quickly into a small beaker placed in a magnetic stirrer, fitted with a magnetic bar. After a few seconds of agitation, 0.4 ml of a solution containing 0.66 ug of adenosine-diphosphate (ADP) per ml was placed in the beaker. After 90 seconds of stirring, two 0.5 ml samples of blood were taken:
- the first was mixed with 0.5 ml of an EDTA-formol solution
- the second was mixed with 0.5 ml of a solution of EDTA only.

The purpose of adding EDTA formol is to stabilize the blood and thus to fix the aggregation whereas EDTA alone causes disaggregation of all the platelet clusters.

After leaving the mixtures at rest for 10 minutes and centrifuging the two mixtures at low speed for 5 minutes in order to separate the red corpuscles, the supernatant platelet-rich plasma (PRP) was removed, diluted and a platelet count was made.

The intensity of the aggregation was determined by the following ratio:

$$\frac{\text{number of platelets in EDTA-formol}}{\text{number of platelets in EDTA}} \times 100 = \text{percentage of non-aggregated platelets.}$$

The blood-platelet aggregation inhibiting action of the product tested improves as the ratio approaches 100.

The results showing the mean percentage of non-aggregated platelets in groups of 5 rats (treated and reference groups) are shown in Table I.

TABLE I

| | ADP TEST | | |
|---|---|---|---|
| PRODUCT | DOSAGE mg/kg | ROUTE* | RESULT |
| Reference group | 3 × 25 | P.O. | 16 ± 4 |
| Derivative No. 1 | — | — | 94 ± 3 |
| Reference group | 3 × 5 | — | 20 ± 11 |
| Derivative No. 1 | — | — | 82 ± 11 |
| Reference group | 3 × 2.5 | — | 23 ± 15 |
| Derivative No. 1 | — | — | 56 ± 17 |
| Reference group | — | — | 8 ± 0 |
| Derivative No. 10 | 3 × 25 | — | 66 ± 2 |
| Derivative No. 10 | 3 × 12.5 | — | 49 ± 11 |
| Reference group | 3 × 10 | — | 8 ± 1 |
| Derivative No. 10 | — | — | 24 ± 5 |
| Reference group | 3 × 60 | — | 11 ± 0 |
| Derivative No. 9 | — | — | 65 ± 7 |
| Reference group | 3 × 100 | — | 13 ± 3 |
| Derivative No. 4 | — | — | 89 ± 1 |
| Reference group | 3 × 100 | — | 3 ± 1 |
| Derivative No. 4 | — | — | 89 ± 4 |
| Reference group | 3 × 100 | — | 4 ± 0 |
| Derivative No. 2 | — | — | 72 ± 12 |
| Reference group | 3 × 100 | — | 4 ± 0 |
| Derivative No. 12 | — | — | 27 ± 5 |
| Reference group | — | — | 2 ± 0 |
| Derivative No. 17 | 3 × 100 | — | 11 ± 3 |
| Derivative No. 20 | 3 × 100 | — | 4 ± 1 |
| Reference group | 3 × 100 | — | 18 ± 1 |
| Derivative No. 6 | — | — | 22 ± 4 |

*Route of administration (b) Determination of collagen-induced blood platelet aggregation 0.10 ml of a solution containing 10 ug of collagen per ml was added to 1.5 ml of citrated blood. With the mixture being agitated, the platelets were counted continually.

The reduction of the number of free platelets over time was continuously monitored and a curve was plotted showing the initial aggregation rate.

The results, representing mean values determined in each group of 5 rats (treated and reference groups), are shown in Table II.

TABLE II

| | COLLAGEN TEST | | |
|---|---|---|---|
| PRODUCT | DOSAGE mg/kg | ROUTE* | RESULT |
| Reference group | 3 × 25 | P.O. | 3.12 ± 0.47 |
| Derivative No. 1 | — | — | 0.14 ± 0.03 |
| Reference group | 3 × 5 | — | 2.17 ± 0.64 |
| Derivative No. 1 | — | — | 0.19 ± 0.04 |
| Reference group | 3 × 2.5 | — | 5.00 ± 1.02 |
| Derivative No. 1 | — | — | 0.60 ± 0.20 |
| Reference group | — | — | 3.92 ± 0.63 |
| Derivative No. 10 | 3 × 25 | — | 0.16 ± 0.07 |
| Derivative No. 10 | 3 × 12.5 | — | 0.54 ± 0.12 |
| Reference group | — | — | 2.00 ± 0.35 |
| Derivative No. 7 | 3 × 100 | — | 0.66 ± 0.18 |
| Derivative No. 8 | 3 × 100 | — | 0.86 ± 0.18 |
| Reference group | 3 × 60 | — | 2.25 ± 0.32 |
| Derivative No. 9 | — | — | 0.11 ± 0.01 |
| Reference group | 3 × 100 | — | 3.41 ± 0.55 |
| Derivative No. 4 | — | — | 0.12 ± 0.02 |
| Reference group | 3 × 100 | — | 4.73 ± 0.55 |
| Derivative No. 4 | — | — | 0.30 ± 0.02 |
| Reference group | 3 × 100 | — | 5.00 ± 1.06 |
| Derivative No. 2 | — | — | 0.51 ± 0.18 |
| Reference group | 3 × 100 | — | 2.25 ± 0.32 |
| Derivative No. 11 | — | — | 0.83 ± 0.02 |
| Reference group | 3 × 100 | — | 2.77 ± 0.32 |
| Derivative No. 14 | — | — | 1.89 ± 0.13 |
| Reference group | 3 × 100 | — | 3.99 ± 0.40 |
| Derivative No. 17 | — | — | 2.22 ± 0.10 |
| Reference group | 3 × 100 | — | 5.01 ± 0.79 |
| Derivative No. 21 | — | — | 3.04 ± 0.22 |
| Reference group | 3 × 100 | — | 11.35 ± 1.01 |
| Derivative No. 18 | — | — | 10.82 ± 0.81 |

*Route of administration (c) Determination of bleeding time

The study of the blood-platelet aggregation inhibiting action also concerned the action of the compound of the invention on bleeding time.

The method used is an adaptation of the method of L. STELLA, M. B. DONATI and G. de GAETANO, Thromb. Res., 1975, 7, 709–716.

The experiment was performed on rats. The compound to be tested was administered to the animals per os in suspension in 10 ml/kg of a 5% aqueous solution of gum arabic 65 hours, 41 hours and 17 hours prior to determination. After anesthetizing the animals with pentobarbital, their tails were cut 5 mm from the ends. The blood was carefully sponged at 15-second intervals, taking care not to touch the wound.

Hemostasis was reached when the bleeding stopped for one minute.

The results representing mean bleeding times in seconds, determined in each group of 5 rats (reference and treated groups), are given in Table III. Times longer than 1200 seconds (20 minutes) were not counted.

TABLE III

| | BLEEDING TIME | | |
|---|---|---|---|
| PRODUCT | DOSAGE mg/kg | ROUTE* | RESULT |
| Reference group | | P.O. | 600 |
| Derivative No. 10 | 3 × 200 | — | 1 200 |
| Derivative No. 2 | 3 × 200 | — | 1 200 |
| Reference group | — | — | 420 |
| Derivative No. 1 | 3 × 25 | — | 1 200 |
| Derivative No. 1 | 3 × 5 | — | 1 080 |
| Reference group | 3 × 12.5 | — | 435 |
| Derivative No. 1 | — | — | 1 200 |
| Reference group | — | — | 780 |
| Derivative No. 3 | 3 × 200 | — | 1 200 |
| Reference group | — | — | 600 |
| Derivative No. 18 | 3 × 200 | — | 1 200 |
| Reference group | | — | 600 |

TABLE III-continued

| | BLEEDING TIME | | |
|---|---|---|---|
| PRODUCT | DOSAGE mg/kg | ROUTE* | RESULT |
| Derivative No. 12 | | — | 1 200 |

*Route of administration (2) Anti-thrombotic activity

This activity was studied by the silk thread experimental thrombosis method.

The principle of this study is an adaptation of the experimental thrombosis method using cardiopulmonary by-pass described by TERUHIKO UMETSU and KAZUKO SANAI (THROMB. HAEMOST., 39, 1, 1978).

The animals' left jugular veins and right external carotid arteries were uncovered (the rats were anesthetized by intraperitoneal injection of pentobarbital.

The arteriovenous shunt consists of a central catheter and two lateral catheters; a white raw silk thread is inserted in the central part and circulation is restored for 20 minutes. After stopping circulation by clamping, the thread is gently withdrawn and weighed immediately. As the average weight of a wet silk thread was previously determined, the weight of the thrombus is determined by evaluation the difference.

The treatment is applied 48 hours, 24 hours and 2 hours before the start of blood flow in the shunt by oral administration of the compound to be tested in suspension in 10 ml/kg of 5% gum arabic, while only the 5% gum arabic solution is administered to the reference group.

The results showing the weight of the thrombus in mg are given in Table IV.

TABLE IV

| ANTI-THROMBOTIC ACTIVITY | | | | |
|---|---|---|---|---|
| PRODUCT | DOSAGE mg/kg | ROUTE* | WEIGHT OF THROMBOSIS IN mg | PERCENTAGE VARIATION |
| Reference group | 3 × 200 | P.O. | 38.56 ± 2.42 | −22 |
| Derivative No. 8 | | — | 29.99 ± 3.05 | |
| Reference group | 3 × 200 | — | 42.65 ± 3.30 | −94 |
| Derivative No. 3 | | — | 2.60 ± 0.24 | |
| Reference group | | — | 36.24 ± 2.05 | |
| Derivative No. 1 | 3 × 25 | — | 6.56 ± 0.51 | −82 |
| Derivative No. 1 | 3 × 12.5 | — | 15.98 ± 1.81 | −56 |
| Reference group | 3 × 5 | — | 40.86 ± 2.02 | −32 |
| Derivative No. 1 | | — | 27.7 ± 2.82 | |
| Reference group | | — | 40.68 ± 1.74 | |
| Derivative No. 2 | 3 × 200 | — | 8.42 ± 3.28 | −79 |
| Derivative No. 10 | 3 × 200 | — | 5.89 ± 0.99 | −86 |
| Reference group | 3 × 200 | — | 35.76 ± 1.76 | −40 |
| Derivative No. 11 | | — | 21.38 ± 2.92 | |

*Route of administration

The toxicological and pharmacological investigations reported above demonstrate the low toxicity of the compounds of the invention, as well as their excellent tolerance and their inhibiting properties on blood-platelet aggregation, and their anti-thrombotic activity, which make them very useful in medical therapeutic applications.

The drug of the invention may be orally administered in the form of tablets, coated tablets, capsules, drops, granules or syrup. The drug can also be provided in the form of suppositories for rectal administration or in the form of solution for injection for parenteral administration.

Each unit dose contains advantageously from 0.005 g to 0.250 g of a derivative of the invention, the daily dosage regimen varying within a range from 0.005 g to 1.00 g active ingredient according to the age of the patient and the severity of the disease to be treated.

Non-limiting examples of pharmaceutical formulations of the medicine of this invention are given below.

(1) Tablets

Derivative No. 1 ... 0.050 g;
Excipient: lactose, icing sugar, rice starch, alginic acid, magnesium stearate.

(2) Coated tablets

Derivative No. 10 ... 0.100 g
Excipient: magnesium stearate, corn starch, gum arabic, shellac, white sugar, glucose, white wax, carnauba wax, paraffin, new cochinealin.

(3) Capsules

Derivative No. 17 ... 0.100 g
Excipient: magnesium stearate, corn starch, lactose (4) Solution for injection Derivative No. 4 ... 0.075 g
isotonic solvent sufficient to make 3 ml (5) Suppositories Derivative No. 21 ... 0.100 g
Semi-synthetic triglycerides sufficient to make 1 suppository.

We claim:

1. A compound of the formula:

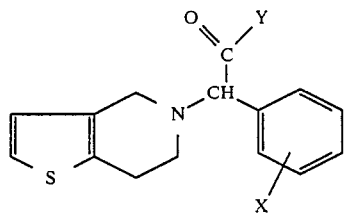

(I)

in which Y represents hydroxyl, an OR group wherein R is a straight or branched lower alkyl radical, or

in which $R_1$ and $R_2$ are each independent of each other and represent hydrogen or a straight or branched lower alkyl group; or $R_1$ and $R_2$ form together with the nitrogen atom to which they are attached a heterocycle selected from the group consisting of pyrrolidino, piperidino, morpholino, piperazino, N-lower alkyl piperazino and N-benzyl piperazino; and X represents hydrogen, a halogen or a lower alkyl radical; and their addition salts with pharmaceutically acceptable mineral or organic acids if Y represents OR groups or

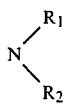

or with mineral bases if Y represents OH, including both enantiomeric forms or their mixture.

2. Methyl α-(4,5,6,7-tetrahydro-thieno(3,2-c)-5-pyridyl)-o.chlorophenyl-acetate.

3. Methyl α-(4,5,6,7-tetrahydro-thieno(3,2-c)-5-pyridyl)phenylacetate.

4. Methyl α-(4,5,6,7-tetrahydro-thieno(3,2-c)-5-pyridyl)-o.fluoro-phenylacetate.

5. Isopropyl α-(4,5,6,7-tetrahydro-thieno(3,2-c)-5-pyridyl)-o.chloro-phenylacetate.

6. Ethyl α-(4,5,6,7-tetrahydro-thieno(3,2-c)-5-pyridyl)-o.chloro-phenylacetate.

7. N,N-dimethyl-[α-(4,5,6,7-tetrahydro-thieno(3,2-c)-5-pyridyl)-o.chlorophenylacetamide.

8. A therapeutic composition having blood-platelet aggregation inhibiting activities and anti-thrombotic activities containing an effective amount of a compound of claim 1, or an addition salt thereof with a pharmaceutically acceptable mineral or organic acid or with mineral bases, or one of the two enantiomers or their mixture and a pharmaceutically acceptable carrier.

9. The composition as claimed in claim 8, in unit dosage form.

10. The composition as claimed in claim 8 or 9 in unit dosage form, each unit containing from 0.10 g to 1.00 g active ingredient.

11. A method of inhibiting platelet aggregation in mammals which comprises administering an effective amount of a composition comprising a compound of claim 1 and a suitable pharmaceutically acceptable carrier.

12. A method of treating or inhibiting thrombosis in mammals which comprises administering to a mammal in need of treatment an effective amount of a composition comprising a compound of claim 1 and a suitable pharmaceutically acceptable carrier.

* * * * *